US007634392B2

(12) United States Patent
Kwun et al.

(10) Patent No.: US 7,634,392 B2
(45) Date of Patent: Dec. 15, 2009

(54) SIMULATION OF GUIDED WAVE REFLECTION SIGNALS REPRESENTING DEFECTS IN CONDUITS

(75) Inventors: Hegeon Kwun, San Antonio, TX (US); Sang-Young Kim, San Antonio, TX (US); Myoung-Seon Choi, Taegu (KR)

(73) Assignee: Southwest Research Institute, San Antonio, TX (US)

( * ) Notice: Subject to any disclaimer, the term of this patent is extended or adjusted under 35 U.S.C. 154(b) by 431 days.

(21) Appl. No.: 10/987,226

(22) Filed: Nov. 12, 2004

(65) Prior Publication Data

US 2005/0182613 A1 Aug. 18, 2005

Related U.S. Application Data

(60) Provisional application No. 60/520,410, filed on Nov. 13, 2003.

(51) Int. Cl.
| *G06F 7/60* | (2006.01) |
| *G06G 7/56* | (2006.01) |
| *G06G 7/48* | (2006.01) |
| *G01B 5/28* | (2006.01) |
| *G01F 1/00* | (2006.01) |
| *G01N 27/00* | (2006.01) |
| *G01N 27/82* | (2006.01) |

(52) U.S. Cl. .............. 703/5; 703/2; 703/7; 702/38; 702/49; 324/71.1; 324/240

(58) Field of Classification Search .......... 73/622, 73/600, 1.82; 703/7, 2, 25, 5; 324/240, 71.1; 702/38, 35, 49

See application file for complete search history.

(56) References Cited

U.S. PATENT DOCUMENTS

| 4,213,183 | A | | 7/1980 | Barron et al. ............... 364/507 |
| 5,581,037 | A | * | 12/1996 | Kwun et al. .................. 73/623 |
| 6,000,288 | A | | 12/1999 | Kwun et al. .................. 73/597 |
| 6,173,074 | B1 | | 1/2001 | Russo ....................... 382/190 |
| 6,250,160 | B1 | | 6/2001 | Koch et al. .................... 73/602 |
| 6,282,962 | B1 | | 9/2001 | Koch et al. .................... 73/602 |
| 6,360,609 | B1 | | 3/2002 | Wooh ......................... 73/602 |
| 6,561,032 | B1 | | 5/2003 | Hunaidi ...................... 73/597 |
| 6,581,014 | B2 | | 6/2003 | Sills et al. ..................... 702/39 |
| 6,766,693 | B1 | * | 7/2004 | Light et al. ................... 73/622 |
| 6,925,881 | B1 | * | 8/2005 | Kwun et al. .................. 73/600 |
| 6,968,727 | B2 | * | 11/2005 | Kwun et al. ................. 73/1.82 |
| 2002/0035437 | A1 | | 3/2002 | Tingley ....................... 702/51 |
| 2002/0149488 | A1 | | 10/2002 | Kechter et al. .............. 340/605 |

OTHER PUBLICATIONS

"Structural Magnetic Strain Model for Magnetorestrictive Transducers". Dapino, et al. IEEE Transactions on Magnetics, vol. 36, No. 3, May 2000.*

* cited by examiner

*Primary Examiner*—Paul L Rodriguez
*Assistant Examiner*—Nithya Janakiraman
(74) *Attorney, Agent, or Firm*—Baker Botts L.L.P.

(57) ABSTRACT

A method and system for simulating defects in conduits, where the defects are detected using long-range guided-wave inspection techniques. The guided wave interaction with a defect is treated as a one-dimensional problem of plane wave reflection from a boundary of different acoustic impedances. The defect waveform is simulated using an electrical transmission line model and inverse fast Fourier transformation.

11 Claims, 4 Drawing Sheets

SIMULATION OF GUIDED WAVE REFLECTION SIGNALS REPRESENTING DEFECTS IN CONDUITS

RELATED PATENT APPLICATION

This application claims the benefit of U.S. Provisional Application No. 60/520,410, filed Nov. 13, 2003 and entitled "SYSTEM AND METHOD FOR SIMULATION OF GUIDED WAVE DEFECT SIGNALS".

GOVERNMENT RIGHTS CLAUSE

The U.S. Government has a paid-up license in this invention and the right in limited circumstances to require the patent owner to license others on reasonable terms as provided for by the terms of Government Contract No. F33615-97-D-5271 awarded by the United States Air Force.

TECHNICAL FIELD OF THE INVENTION

This invention relates to methods and systems for using guided waves to detect defects in conduits, such as pipes, and more particularly to simulating signals reflected from such defects.

BACKGROUND OF THE INVENTION

Long-range guided-wave inspection is an effective method for rapidly surveying long structures for defects such as cracks and corrosion pits. Using this method, a short pulse of guided waves at a typical frequency of below 100 kHz is launched within a structure being tested. This incident pulse is reflected from a geometric irregularity in the structure. The reflected signals are detected in a pulse-echo mode.

This method of inspection is presently in practical use for inspection of piping networks in processing plants, and oil and gas transmission pipelines. When applied to piping, the guided wave technique can typically detect defects as small as 2-3% relative to the pipe wall cross sectional area, over a length of 30 meters on either side of a test probe position. In addition to detecting the presence or absence of defects, the defect signals resulting from long-range guided-wave inspection can be used to characterize defects. For example, defects can be characterized in terms of planar or volumetric, depth, axial extent, and circumferential extent.

In order to characterize defects from the defect signals, it is necessary to understand how defect signal waveforms relate to defect characteristics. When the waveform-defect characteristic relationship is established, algorithms relating these relationships may be developed. Modeling simulation of waveforms of defect signals from arbitrary-shaped defects is necessary for establishing relationships between the defect signal characteristics and the defect characteristics.

There are several known techniques for modeling guided-wave interaction with defects, such as finite element analysis, boundary element analysis, and related hybrid methods. Because these methods are tedious and computationally intensive, their use has been limited to two-dimensional modeling of guided wave interactions with simple geometry defects, such as a notch that is infinitely long in a plate or completely circumferential in a pipe. Presently, complex and expensive three-dimensional modeling is required to handle interactions with finite-sized and arbitrary-shaped defects and to simulate defect waveforms.

BRIEF DESCRIPTION OF THE DRAWINGS

A more complete understanding of the present embodiments and advantages thereof may be acquired by referring to the following description taken in conjunction with the accompanying drawings, in which like reference numbers indicate like features, and wherein.

DETAILED DESCRIPTION OF THE INVENTION

The method and system described herein are directed to simulating waveforms reflected from a defect in a conduit, where the incident wave is a long range guided wave. These reflected signals are referred to herein as "defect signals".

The conduit is typically piping, as in the examples used herein. However, the conduit need not be circular in diameter. For example, the conduit could be tubing having a rectangular cross section. The method is particularly useful for generating simulated defect signals in piping having arbitrarily shaped defects, such as loss of pipe wall material due to erosion, corrosion and gouging.

The method is easy and computationally fast. It may be implemented with programming for conventional computing devices, such as personal computers.

Figure 1:
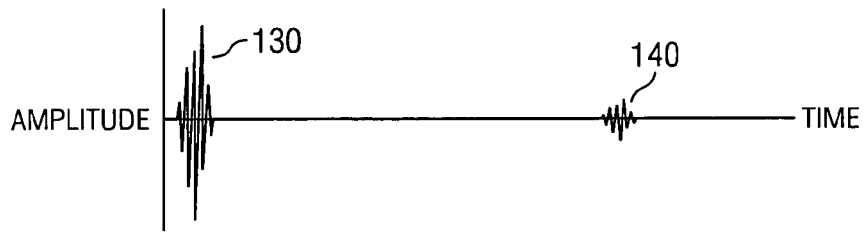
FIG. 1 illustrates a transmitted incident pulse and a reflected defect signal from an arbitrarily shaped volumetric defect in a pipeline.

FIG. 1 illustrates a transmitted incident pulse 130, and a defect signal 140 reflected from a defect in a conduit. These signals are represented in terms of amplitude and time.

The incident pulse 130 and the defect signal 140 are representative of signals transmitted by the transmitter and detector elements of a guided wave inspection system, such as is known in the art. The transmitter delivers the incident pulse 130 into a conduit, and after a round trip excursion time, the defect signal 140 is received by the detector.

As explained below, the method described herein simulates a reflected defect signal, such as signal 140, from any arbitrarily shaped defect. The method is performed by treating guided wave interactions with defects as a one dimensional problem of plane wave reflections from a boundary of different acoustic impedances. A waveform representing a defect is simulated using an electrical transmission line model and a fast Fourier transform (FFT) techniques.

Figure 2:
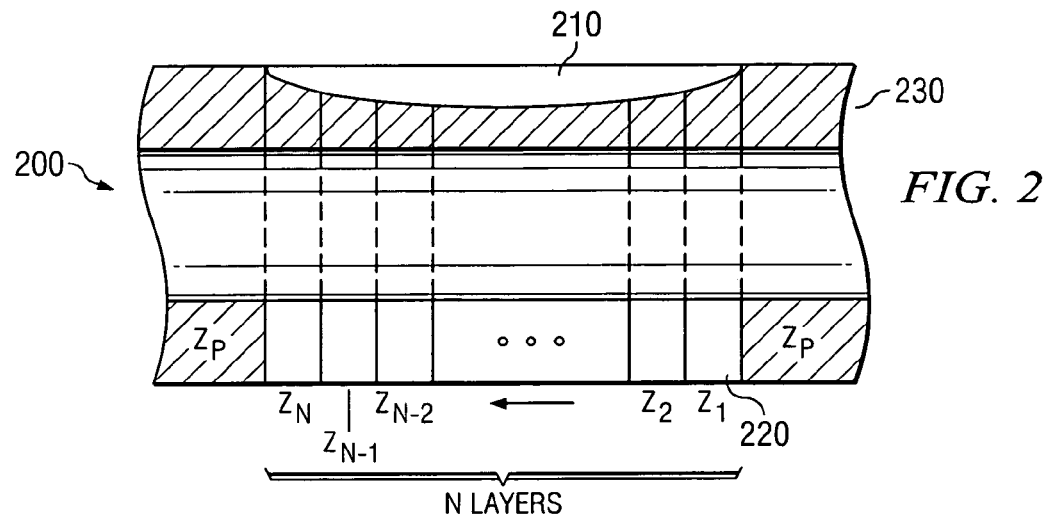
FIG. 2 is a lengthwise cross-sectional view of a pipe having an internal defect, and further illustrates a transmission line model of the defective region.

FIG. 2 illustrates a longitudinal cross-section of a pipe 200. A volumetric defect 210 is present in the pipe wall 230. In the example of FIG. 2, the defect is "bowl" shaped corrosion defect, but a feature of the invention is that a defect having any shape may be simulated.

FIG. 2 further illustrates how the defective region of pipe 200 may be represented with an electrical transmission line model. This model is well known in the art of electrical transmission lines.

Specifically, the defective region of the pipe 200 is represented as having N layers 220. Each layer 220 has an associated acoustic impedance, $Z_1, Z_2, \ldots Z_N$. The impedance of the pipe 200 without defects is represented as $Z_p$. As explained below, these impedances may be used to compute an overall effective input impedance of the defective region 210.

Figure 3:
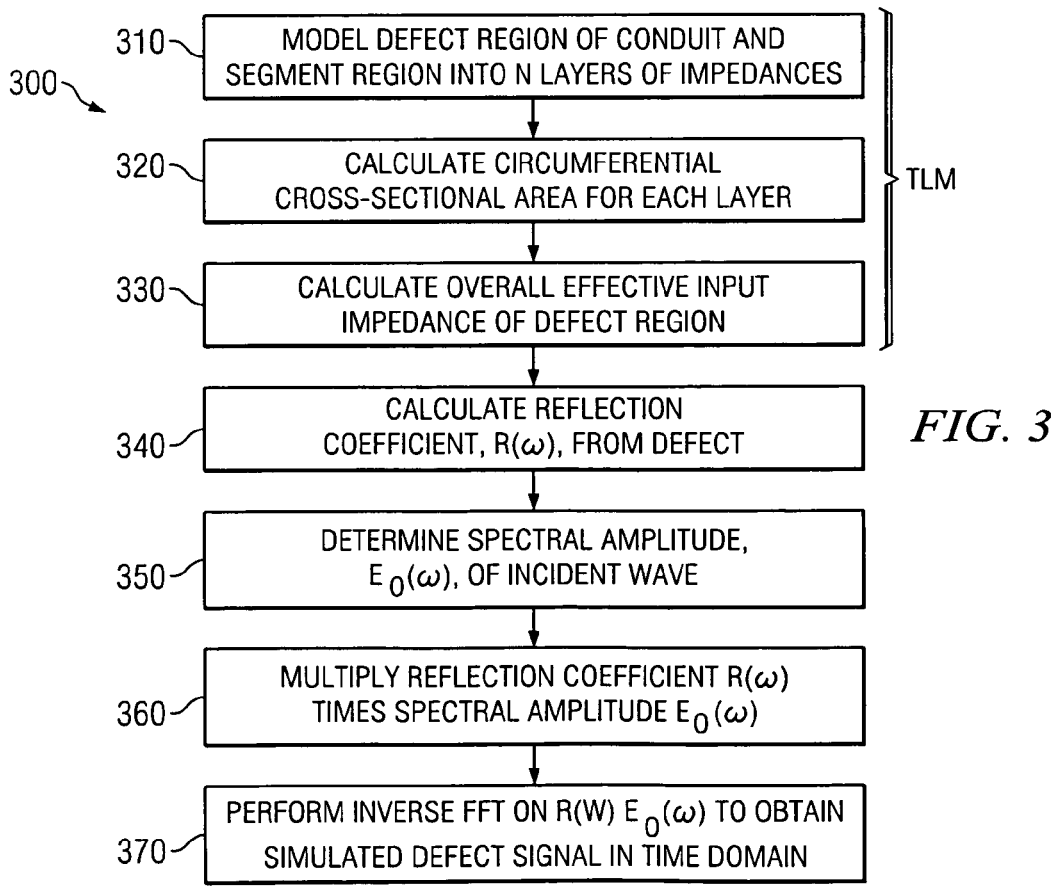
FIG. 3 is a flow diagram representing steps of the method of the present invention.

FIG. 3 is a flow diagram representing the simulation method in accordance with the invention. Steps 310-330 involve use of the transmission line model to calculate an overall effective impendence of the defective region of the pipe. tep 310 is consistent with the model illustrated in FIG. 2, and is modeling a section of pipe (or other conduit) that contains a volumetric defect. As stated above, the pipe model may have any shape or size of defect. The defective region is modeled as having N cross-sectional layers. Each of the N layers has an associated acoustic impedance, $Z_n$.

Step 320 is calculating a circumferential cross-sectional area, $A_n$, for each of the N layers. The acoustic impedance, $Z_n$, of each layer is treated as being proportional to the respective cross-sectional area, $A_n$, of each layer.

Step 330 is calculating an overall effective input impedance, $Z_d^{eff}$, of the defective region, over the band of frequency spectrum of the incident pulse. This overall effective input impedance is equal to the input impedance of the overall layer, $Z_{n+1}^I$. It may be calculated using the recursion relation for the input impedance of two successive layers:

$$Z_{n+1}^I = Z_n[Z_n^I + jZ_n \tan(k\zeta_n)]/[Z_n + jZ_n^I \tan(k\zeta_n)],$$

where $Z_{N+1}^I$ is the complex input impedance of layers up to n; k is the wave number of the incident wave; $\zeta_n$ is the thickness of the nth layer, and $Z_1^I = Z_p$ is the acoustic impedance of the pipe without defects. Further, the acoustic impedance of each nth layer, $Z_n$, is determined by the relation:

$$Z_n = \rho V A_n,$$

where $\rho$ is the density of the pipe material, V is the velocity of guided waves in the pipe material, and $A_n$ is the cross-sectional area of the nth layer.

Step 340 is computing a reflection coefficient, $R(\omega)$, from the defect at angular wave frequency, $\omega$, over the band of frequency spectrum contained in the transmitted incident guided wave. The effective input impedance and the impedance of the pipe without defects are input parameters to this calculation. The following equation is used:

$$R(\omega) = (Z_d^{eff} - Z_p)/(Z_d^{eff} + Z_p)$$

Step 350 is determining the spectral amplitude, $E_0(\omega)$, of the incident signal at each frequency. This may be accomplished by performing a Fast Fourier Transform (FFT) on a representation of the incident signal in the time domain.

Step 360 is multiplying the computed reflection coefficient, $R(\omega)$, times the spectral amplitude of the incident wave signal, $E_0(\omega)$.

Step 370 is performing an inverse Fast Fourier Transform on the product obtained in Step 360. The result is a simulated defect signal waveform in a time domain representation.

Figure 4A:
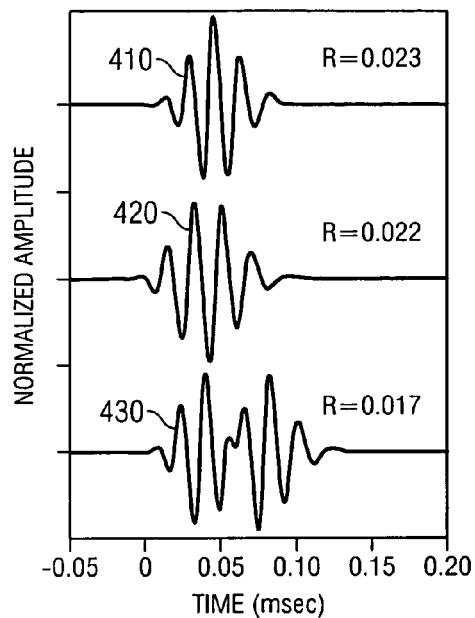
FIGS. 4A and 4B are three comparisons of simulated and measured signals, reflected from three different defects, using a 64 KHz incident pulse.
Figure 4B:
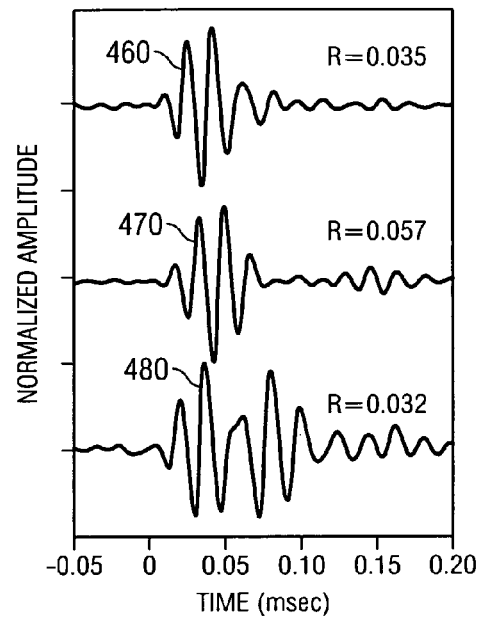

FIGS. 4A and 4B illustrate the effectiveness of the invention. FIG. 4A is a time domain representation of three defect signals 410, 420, 430, which were produced using the above-described simulation method. Each defect signal is from a differently shaped defect. FIG. 4B is a time domain representation of three defect signals 460, 470, 480, each measured from a defect having the same shape and size as used to simulate the corresponding signal in FIG. 4A.

The incident wave (simulated and actual) was a 64 kHz pulse of an L(O,2) wave. The incident pulse has a waveform that is approximately the same as the upper simulated waveform 410 shown in FIG. 4A. The shape of the simulated and actual signals agree well, indicative of the effectiveness of the above-described method.

Figures 1, 6A:
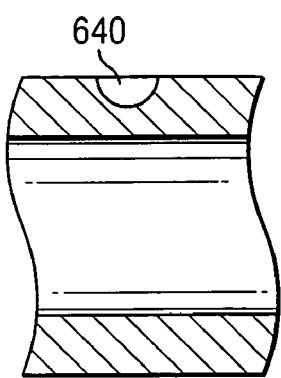
FIGS. 6A, 6B and 6C are cross-sectional views of pipe defects, used for the simulated and measured signal comparisons of FIGS. 4A and 4B and FIGS. 5A and 5B.
Figures 2, 6A:
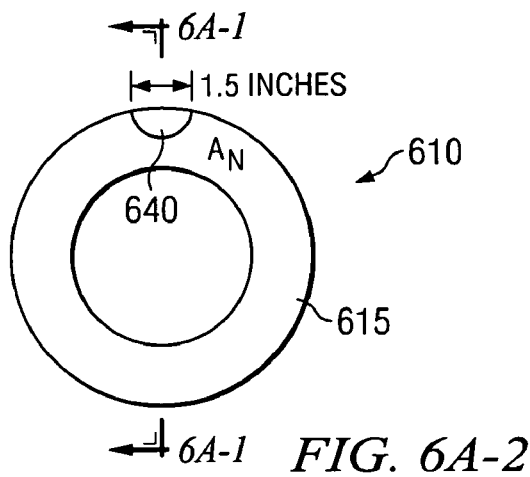
Figures 1, 6B:
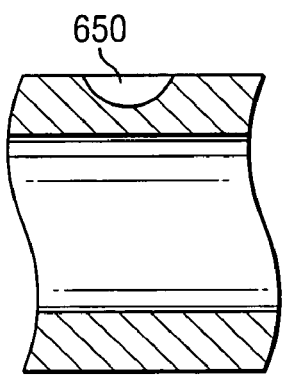
Figures 2, 6B:
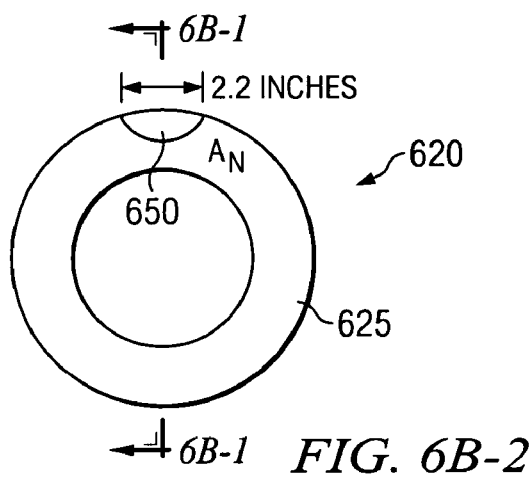
Figures 1, 6C:
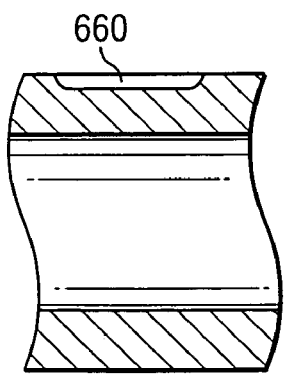
Figures 2, 6C:
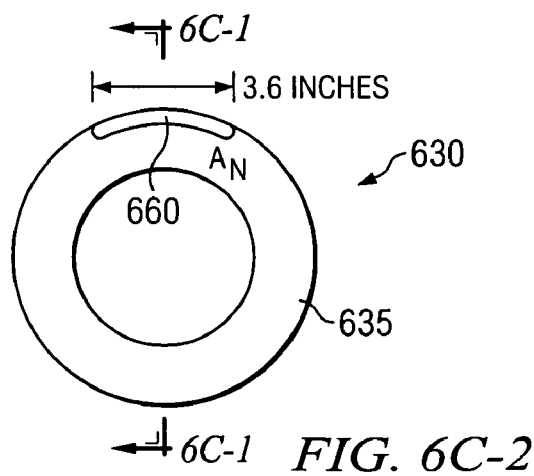

The defects used for simulating and measuring the waveforms of FIGS. 4A and 4B are illustrated in FIG. 6A, 6B and 6C. These figures are longitudinal and lateral cross-sectional views of pipes 610, 620, 630, depicting defects 640, 650, 660 in the pipe walls 615, 625, 635 used for simulating and measuring guided-wave defect signals. The pipes 610, 620, 630 have a 4.5 inch outside diameter with a wall 615, 625, 635 having a thickness of 0.337 inches. The defects 640, 650, 660 are circular corrosion wall-loss areas.

The defect 640 of FIG. 6A is approximately 1.5 inches in diameter and has a depth of about half of the wall thickness. The defect 650 of FIG. 6B is approximately 2.2 inches in diameter and has a depth of about half of the wall thickness. The defect 660 of FIG. 6C is elliptical in shape, approximately 4.1 inches long, and has a depth of about one quarter of the wall thickness.

The defect shown in FIG. 6A resulted in the top simulated waveform 410 in FIG. 4A and the top actual waveform 460 shown in FIG. 4B. The defect shown in FIG. 6B resulted in the middle simulated waveform 420 in FIG. 4A and the middle actual waveform 470 shown in FIG. 4B. The defect shown in FIG. 6C resulted in the bottom simulated waveform 430 in FIG. 4A and the bottom actual waveform 480 shown in FIG. 4B.

Figure 5A:
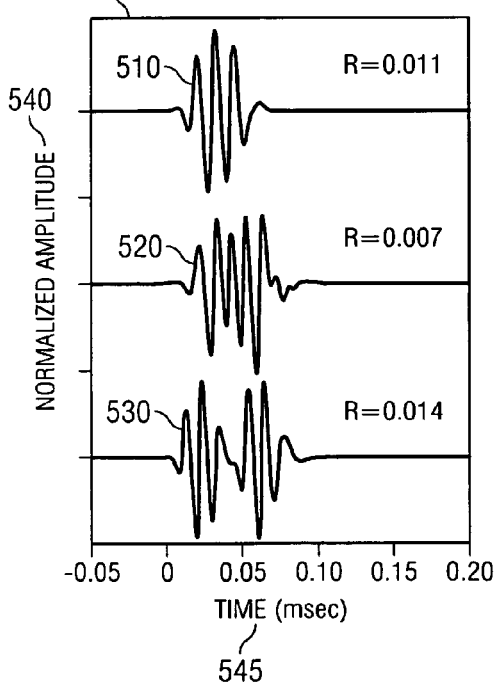
FIGS. 5A and 5B are three comparisons of simulated and measured signals, reflected from three different defects, using a 100 KHz incident pulse.
Figure 5B:
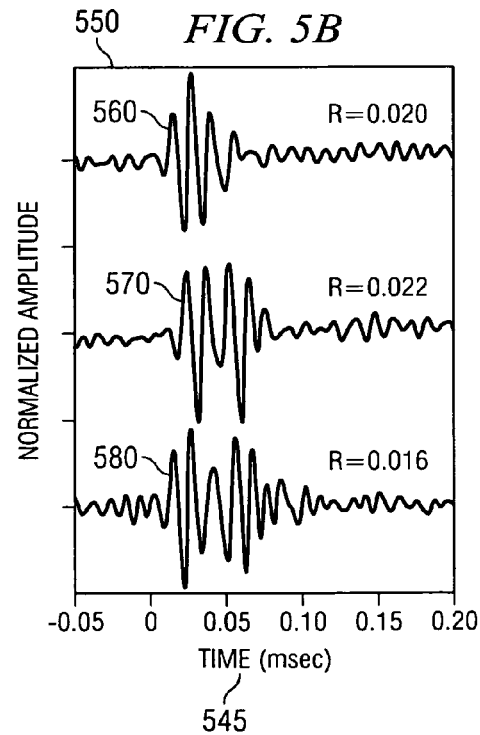

FIGS. 5A and 5B are similar to FIGS. 4A and 4B, with the difference being that the incident pulse is a 100 KHz pulse of the same L(0,2) wave.

FIGS. 4A, 4B, 5A, and 5B further show the calculated (FIGS. 4A and 5A) and measured (FIGS. 4B and 5B) reflection coefficients, r. Here, r is defined as the peak amplitude of the defect signal divided by the peak amplitude of the incident pulse. Although the simulated and actual quantitative values of the reflection coefficients are at some variance, a suitable correction factor may be applied to correct for the attenuation in the relevant signals.

The invented method applies to defects whose extent in the lengthwise (axial) direction of the pipe is equal to or larger than one-fourth of the wavelength at the center frequency of the incident wave. For volumetric effects having an axial extent less than one-fourth of the wavelength and for planar defects such as cracks, the formula for wave reflection at boundaries of two different impedances may be used:

$$R(\omega) = (Z_d - Z_p)/(Z_d + Z_p),$$

where $Z_d = \rho V A_d$, and $A_d$ is the minimum circumferential cross-sectional area of the pipe wall in the defect region.

An important advantage of the present invention over other methods is that it simulates defect signals quickly and easily without extensive computation and mesh preparation, as required by other methods.

Figure 7:
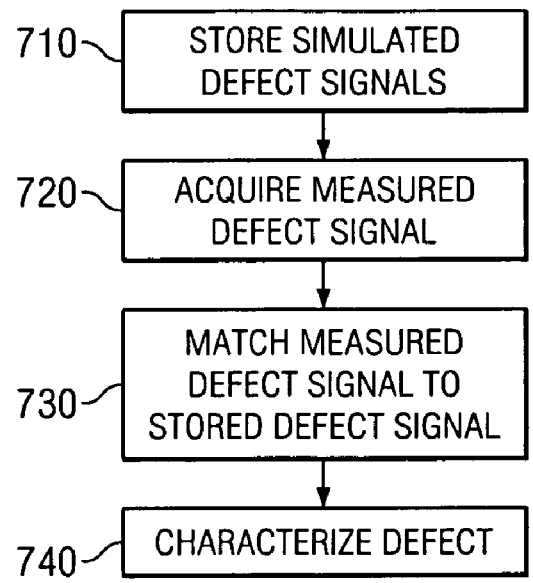
FIG. 7 illustrates a method of characterizing defects in a conduit in accordance with the invention.

FIG. 7 illustrates a method for characterizing a defect in a conduit in accordance with the invention. As indicated above, the above-described method is especially useful for inspecting networks of pipes. The method may be implemented using conventional data storage, processing, and input devices.

Step 710 is storing a set of simulated defect signals. These signals are simulated, using a variety of simulated defects in conduits similar to a conduit to be inspected.

Step 720 is receiving a measured defect signal from the conduit under inspection. Known guided wave transducers and detectors may be used to acquire measured signals from actual defects. There are various approaches to long range guided wave testing, and various types of probes may be used for such testing. Examples of suitable probes are magnetostrictive sensor probes and piezoelectric transducer probes. The measured signal is digitized and input to a processing device.

Step 730 is matching the measured signal to a stored simulated signal. Various data processing techniques may be used to find a best match. For example, known techniques of pattern recognition may be used for such comparisons.

Step 740 is characterizing the actual defect, based on the result of the matching step. For example, if the best match of the measured defect signal is to a simulated signal from a defect having a certain size and shape, the actual defect may be assumed to have a similar size and shape.

Figure 8:
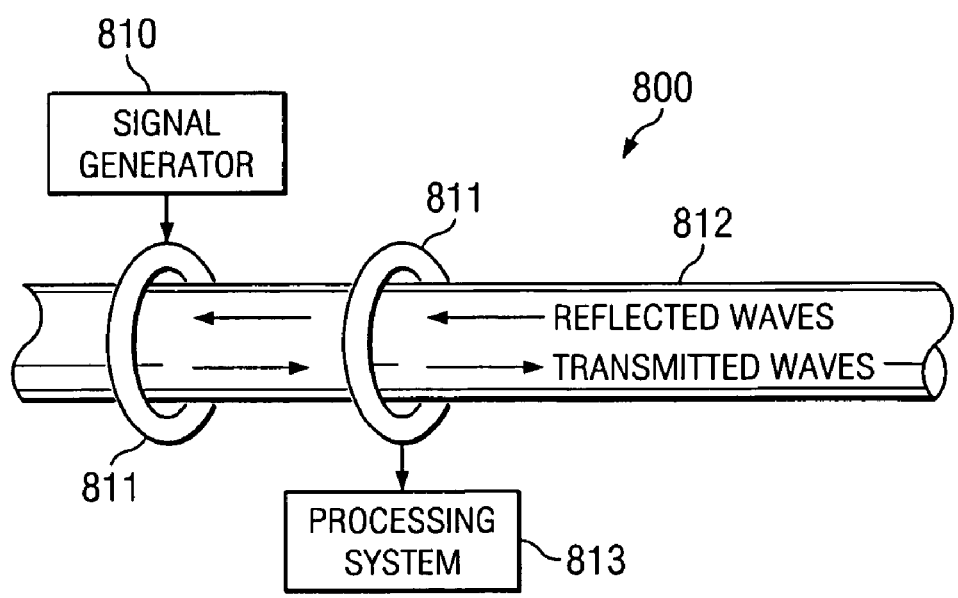
FIG. 8 illustrates a conduit inspection system for implementing the method of FIG. 7.

FIG. 8 illustrates one example of a long range guided wave system 800, suitable for implementing the method of FIG. 7. System 800 uses magnetostrictive probes 811, which generate and detect mechanical waves in ferromagnetic material. Each probe 811 comprises an inductive coil encircling the pipe 812 and a bias magnet. A time-varying magnetic field is applied to the pipe 812 by the transmitting coil 811 and this generates an elastic wave in the pipe due to the magnetostrictive effect. The waves propagate along the pipe 812 in both directions. The receiving magnetostrictive probe 811 detects changes in magnetic induction in the pipe due to the inverse magnetostrictive effect when the waves pass through. This technique is described in U.S. Pat. No. 5,581,037, entitled "Nondestructive Evaluation of Pipes and Tubes Using Magnetostrictive Sensors," to Kwun and Teller, assigned to Southwest Research Institute (San Antonio, Tex.), and incorporated by reference herein.

The probe outputs are delivered to a processing system 813, which has memory and processing components suitable for implementing the method described herein. Processing system 813 is programmed with instructions for carrying out the method of FIG. 7, and may further be programmed with a suitable user interface for receiving operation commands and displaying results to an operator via a display.

Although the present invention has been described in detail with reference to certain preferred embodiments, it should be apparent that modifications and adaptations to those embodiments might occur to persons skilled in the art without departing from the spirit and scope of the present invention.

What is claimed is:

1. A method of using a computer system to model the magnetostrictive effect when a guided wave incident signal is reflected within a conduit having a defective region; comprising:

modeling the defective region as having a succession of n layers along a length of the pipeline, each layer having a cross-sectional area that varies from the cross-sectional area of the pipeline;

calculating a cross sectional area of each of the layers;

calculating an impedance of each layer as the product of the density of the pipe material, the velocity of acoustic waves in the material, and the cross-sectional area of the layer;

calculating an overall complex input impedance of the region;

wherein the calculating step is performed by recursively calculating the input impedance of each two successive layers as:

$$Z_{n+1}^I = Z_n[Z_n^I + jZ_n \tan(k\zeta_n)]/[Z_n + jZ_n^I \tan(k\zeta_n)],$$

where $Z_{N+1}^I$ is the complex input impedance of layers up to n; k is the wave number of the incident signal; $\zeta_n$ is the thickness of the nth layer, and $Z_1^I = Z_p$ is the acoustic impedance of the pipe without defects;

calculating a reflection coefficient based on the overall input impedance and the input impedance of a conduit without defect;

calculating a spectral amplitude of the incident signal;

using the reflection coefficient as a transfer function of the spectral amplitude of the incident signal, thereby obtaining a frequency domain representation of the defect signal data; and storing the defect signal data in memory of the computer system.

2. The method of claim 1, further comprising the step of performing an inverse fast Fourier transform on the frequency domain representation of the defect signal, thereby obtaining a time domain representation of the defect signal.

3. The method of claim 1, wherein the incident signal has a range of frequencies, and wherein the overall input impedance, the reflection coefficient, and the spectral amplitude are calculated at each frequency.

4. The method of claim 1, wherein the reflection coefficient is expressed as a ratio based on the overall input impedance and the input impedance of the conduit without defects.

5. The method of claim 1, wherein the reflection coefficient is calculated as:

$$R(\omega) = (Z_d^{eff} - Z_p)/(Z_d^{eff} + Z_p),$$

where $Z_d^{eff}$ is the overall input impedance of the layers, and $Z_p$ is the input impedance of the conduit without defect.

6. The method of claim 1, wherein the step of using the reflection coefficient as a transfer function is performed by multiplying the reflection coefficient times the spectral amplitude of the incident signal.

7. A processing system for identifying a real world defect in a conduit, comprising:

a memory programmed to store a set of simulated defect signals, wherein each defect signal simulates a signal reflected as a result of the magnetostrictive effect in the conduit;

wherein each simulated defect signal is calculated by:

modeling the defective region as having a succession of n layers along a length of the pipeline, each layer having a cross-sectional area that varies from the cross-sectional area of the pipeline;

calculating a cross sectional area of each of the layers;

calculating an impedance of each layer as the product of the density of the pipe material, the velocity of acoustic waves in the material, and the cross-sectional area of the layer;

calculating an overall complex input impedance of the region;

wherein the calculating step is performed by recursively calculating the input impedance of each two successive layers as:

$$Z_{n+1}^I = Z_n[Z_n^I + jZ_n \tan(k\zeta_n)]/[Z_n + jZ_n^I \tan(k\zeta_n)],$$

where $Z_{N+1}^I$ is the complex input impedance of layers up to n; k is the wave number of the incident signal; $\zeta_n$ is the thickness of the nth layer, and $Z_1^I=Z_p$ is the acoustic impedance of the pipe without defects;

calculating a reflection coefficient of the simulated defect signal based on the overall input impedance and a value representing the input electrical impedance of a conduit without defect;

calculating a spectral amplitude of an incident signal; and using the reflection coefficient as a transfer function of the spectral amplitude of the incident signal, thereby obtaining a data representation of the simulated defect signal;

a processor programmed to receive a measured defect signal from the real world defect;

wherein the measured defect signal is acquired by reflecting a guided wave incident signal from the real world defect; and wherein the processor is further programmed to match the measured defect signal to a simulated defect signal.

8. The processing system of claim 7, wherein the processor is further programmed to output data representing characteristics of the defect, based on the results of the matching step.

9. The processing system of claim 7, wherein the processor is further programmed to perform an inverse fast Fourier transform on the frequency domain representation of the defect signal, thereby obtaining a time domain representation of the defect signal.

10. A computer-implemented method of modeling a defect in a pipeline, the pipeline having a known cross-sectional area in non-defective regions, comprising:

modeling the defect as a region of the pipeline having a succession of n layers along a length of the pipeline, each layer having a cross-sectional area that varies from the cross-sectional area of the pipeline;

calculating a cross sectional area of each of the layers;

calculating an impedance of each layer as the product of the density of the pipeline, the velocity of acoustic waves in the material, and the cross-sectional area of the layer;

calculating an overall complex input impedance of the region, using an electrical transmission line input impedance calculation;

wherein the calculation is performed by recursively calculating the input impedance of each two successive layers as:

$$Z_{n+1}^I = Z_n[Z_n^I + jZ_n \tan(k\zeta_n)]/[Z_n + jZ_n^I \tan(k\zeta_n)],$$

where $Z_{N+1}^I$ is the complex input impedance of layers up to n; k is the wave number of the incident wave; $\zeta_n$ is the thickness of the nth layer, and $Z_1^I=Z_p$ is the acoustic impedance of the pipe without defects; and storing the complex input impedance of the region in memory of the computer.

11. A processing system for modeling a defect in a pipeline, the pipeline having a known cross-sectional area in non-defective regions, comprising:

a processor programmed to calculate defect input impedance values by:

modeling the defect as a region of the pipeline having a succession of n layers along a length of the pipeline, each layer having a cross-sectional area that varies from the cross-sectional area of the pipeline;

calculating a cross sectional area of each of the layers;

calculating an impedance of each layer as the product of the density of the pipeline, the velocity of acoustic waves in the material, and the cross-sectional area of the layer;

calculating an overall complex input impedance of the region, using an electrical transmission line input impedance calculation;

wherein the calculation is performed by recursively calculating the input impedance of each two successive layers as:

$$Z_{n+1}^I = Z_n[Z_n^I + jZ_n \tan(k\zeta_n)]/[Z_n + jZ_n^I \tan(k\zeta_n)],$$

where $Z_{N+1}^I$ is the complex input impedance of layers up to n; k is the wave number of the incident wave; $\zeta_n$ is the thickness of the nth layer, and $Z_1^I=Z_p$ is the acoustic impedance of the pipe without defects.

\* \* \* \* \*